US012657335B2

(12) United States Patent　　　　(10) Patent No.:　　US 12,657,335 B2

Stockert et al.　　　　　　　　　　(45) Date of Patent:　　*Jun. 16, 2026

(54) DATA AGGREGATION BASED ON DISPARATE LOCAL PROCESSING OF REQUESTS

(71) Applicant: Health2047, Inc., Menlo Park, CA (US)

(72) Inventors: Jack Stockert, Los Altos, CA (US); Charles Aunger, Hayward, CA (US)

(73) Assignee: Health2047, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/360,507

(22) Filed: Jul. 27, 2023

(65) Prior Publication Data

US 2024/0095398 A1　　Mar. 21, 2024

Related U.S. Application Data

(63) Continuation of application No. 16/779,367, filed on Jan. 31, 2020, now Pat. No. 11,714,915.

(60) Provisional application No. 62/800,209, filed on Feb. 1, 2019.

(51) Int. Cl.
| | |
|---|---|
| *G16H 50/30* | (2018.01) |
| *G06F 19/00* | (2018.01) |
| *G06F 21/62* | (2013.01) |
| *G06N 3/08* | (2023.01) |
| *G16H 10/60* | (2018.01) |
| *G16H 15/00* | (2018.01) |
| *G16H 50/70* | (2018.01) |

(52) U.S. Cl.
CPC ........... *G06F 21/6245* (2013.01); *G06N 3/08* (2013.01); *G16H 10/60* (2018.01); *G16H 15/00* (2018.01); *G16H 50/70* (2018.01)

(58) Field of Classification Search
CPC ........ G16H 50/20; G16H 50/50; G06F 17/18; G06N 20/00
See application file for complete search history.

(56) References Cited

U.S. PATENT DOCUMENTS

| | | | |
|---|---|---|---|
| 9,393,418 | B2 | 7/2016 | Giuffrida et al. |
| 9,501,624 | B2 | 11/2016 | Vishnubhatla et al. |
| 10,784,000 | B2 | 9/2020 | Wu et al. |
| 11,210,418 | B2 | 12/2021 | Stockert et al. |
| 11,322,248 | B2 | 5/2022 | Grantcharov et al. |
| 11,523,773 | B2 | 12/2022 | Orr et al. |
| 11,714,915 | B2 | 8/2023 | Stockert et al. |
| 2011/0282861 | A1 | 11/2011 | Bergstraesser et al. |
| 2017/0103167 | A1 | 4/2017 | Shah |

(Continued)

*Primary Examiner* — Maroun P Kanaan

(74) *Attorney, Agent, or Firm* — Knobbe, Martens, Olson & Bear, LLP

(57)　　　　ABSTRACT

Systems and methods for data aggregated based on disparate local processing of requests. One of the methods includes receiving a request associated with analyzing medical data, the request specifying one or more constraints; accessing index information, and identifying one or more medical providers storing medical data responsive to the request; instructing, for each medical provider, compute systems controlled by the medical provider to perform the request; receiving, from the medical providers, results associated with the request, and aggregating the results; providing the aggregated results in response to the request.

18 Claims, 8 Drawing Sheets

(56)  References Cited

U.S. PATENT DOCUMENTS

| | | | |
|---|---|---|---|
| 2017/0300634 A1 | 10/2017 | Chiang et al. | |
| 2018/0358117 A1* | 12/2018 | Neagle | A61B 5/0015 |
| 2019/0146458 A1 | 5/2019 | Roh et al. | |
| 2020/0152226 A1 | 5/2020 | Anushiravani et al. | |
| 2020/0227160 A1* | 7/2020 | Youngblood | G16H 40/20 |
| 2020/0251225 A1* | 8/2020 | Murrish | G06F 16/951 |
| 2021/0076966 A1 | 3/2021 | Grantcharov et al. | |
| 2022/0253552 A1 | 8/2022 | Stockert et al. | |

* cited by examiner

300

302
Receive request to execute query, the query comprising constraints

304
Authenticate request

306
Identify providers storing data associated with request, the data being authorized for responding to the request 308
Provide instructions associated with request to compute systems of identified providers 310
Route results received from compute systems

Figure 4:
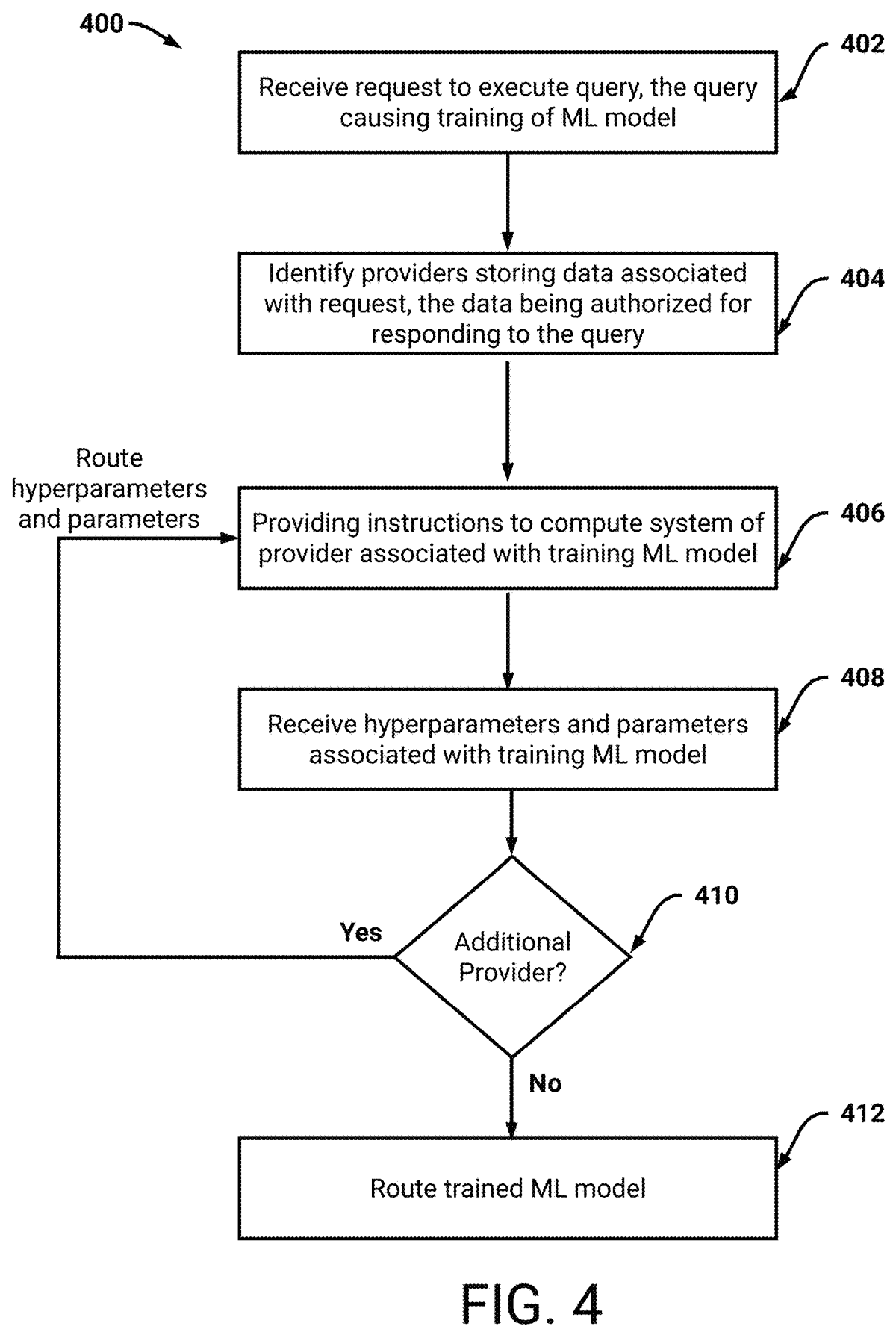

400 ⟍

```
                        ┌──────────────────────────────────────┐   402
                        │  Receive request to execute query,    │⟋
                        │  the query causing training of ML      │
                        │  model                                 │
                        └──────────────────────────────────────┘
                                        │
                                        ▼
                        ┌──────────────────────────────────────┐   404
                        │  Identify providers storing data       │⟋
                        │  associated with request, the data     │
                        │  being authorized for responding to    │
                        │  the query                             │
                        └──────────────────────────────────────┘
                                        │
          Route                          ▼
   hyperparameters         ┌──────────────────────────────────────┐   406
   and parameters          │  Providing instructions to compute     │⟋
        │                  │  system of provider associated with    │
        └─────────────────▶│  training ML model                     │
                           └──────────────────────────────────────┘
                                        │
                                        ▼
                        ┌──────────────────────────────────────┐   408
                        │  Receive hyperparameters and           │⟋
                        │  parameters associated with training   │
                        │  ML model                              │
                        └──────────────────────────────────────┘
                                        │
                                        ▼
                                     ╱─────╲   410
                              Yes   ╱ Additional╲⟋
        ┌───────────────────────── ╲ Provider? ╱
        │                           ╲─────╱
                                        │
                                        │ No
                                        ▼
                        ┌──────────────────────────────────────┐   412
                        │  Route trained ML model                │⟋
                        └──────────────────────────────────────┘
```

Receive secure integration request from provider

504

Integrate provider, and store indexed medical information stored by provider

506

Store data authorization information

508

Determine quality metrics associated with provider

DATA AGGREGATION BASED ON DISPARATE LOCAL PROCESSING OF REQUESTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure relates to systems and techniques for security, data integration, and visualization. More specifically, this disclosure relates to processing of medical data.

BACKGROUND

Medical data may generally be stored in electronic medical record (EMR) systems located at hospitals. These EMR systems may store medical data for different patients, such that medical professionals may access the medical data to administer medical care. For example, an EMR system may provide a front-end user interface for entry of medical data related to a specific patient. The EMR system may further enable review of entered medical data, medical images, and so on. Additionally, EMR systems may further store information generated by medical professionals, such as notes related to administering medical care.

Access to medical data may be tightly constrained. For example, medical professionals may be required to authenticate prior to accessing EMR systems. An EMR system may provide global access to stored medical data based on an authenticated user name and password of a medical professional. An EMR system may also provide access to stored medical data to which a medical professional is specifically authenticated. For example, a medical professional may view medical data of the medical professional's patients. In this example, the medical professional may be restricted from access to other medical data.

Commonly, hospitals may have data rights agreements in place with patients. These data rights agreements may outline approved uses of patients' medical data. For example, a data rights agreement may indicate that portions of a patient's medical data may be utilized for research purposes. The portions may be required to be anonymized, such the patient's personally identifiable information is removed. It may be appreciated that insights may be extracted based on analyzing this medical data. However, due to technical considerations relating to access rights, such analyses may be technically infeasible at present. For example, data access rights may be restricted to certain use cases. Data access rights may also be restricted to certain medical professionals, and so on.

SUMMARY

Particular embodiments of the subject matter described in this specification can be implemented so as to realize one or more of the following advantages. Medical data may be locally stored by medical providers and outside users may extract insights from such medical data. Advantageously, the insights may be extracted without the users' access to the medical data itself. As will be described, a system described herein may route queries from outside users to medical providers storing medical data responsive to the queries. A query may indicate a request for an analysis to be performed on medical data which satisfies particular constraints. The medical providers may then process the queries, thus limiting direct access to medical data by the outside users. Examples of medical providers may include hospitals, medical research institutions, and so on. In this way, the techniques described herein may ensure adherence to strict medical data rights privileges while enabling technical schemes to leverage the medical data.

It may be appreciated that ensuring privacy of medical data is of particular importance to medical providers. Indeed, due to restrictions regarding usage of such medical data, medical providers may tightly restrict access to their stored medical data. However, the rise of complex modeling techniques has enabled deep insights to be extracted from aggregations of medical data. For example, efficacies of treatment plans may be ascertained. As another example, risk factors related to certain ailments may be identified and/or validated. As another example, a model may enable time-sensitive identifications of ailments which may be affecting one or more patients. Example modeling techniques may include machine learning models. For example, a machine learning model may be trained based on datasets generated from medical data.

Current schemes to utilize such medical data fail to ensure that all access is authorized. For example, a medical provider may have to provide (e.g., via the internet) stored medical data for utilization by outside users (e.g., researchers). The outside users may then perform particular analyses using the medical data. However, once the medical data leaves the control of the medical provider there may be no technological scheme to monitor use of the medical data. Additionally, the medical provider's medical data may be replicated across systems utilized by outsider users. Without safeguards to medical data, medical providers may thus limit an extent to which complex models may be executed across large datasets.

As will be described, a system may receive queries from outside users regarding analyses to be performed. An example query may indicate features of medical data, patients, and so on, which are to be utilized in an analysis. The system may rapidly identify medical providers storing medical data responsive to the queries. For example, the system may store index information associated with medical data stored by multitudes of medical providers. The system may route a query for local processing to medical providers storing responsive medical data. In this way, the techniques described herein ensure, in some embodiments, that medical data is not required to be moved, copied, reproduced, or repurposed beyond the local control of the medical providers. Utilizing local computing systems, the medical providers may provide results associated with a requested analysis. Advantageously, a query may identify, or provide, a particular model to be utilized in a requested analysis. The system may then optionally aggregate the results received from the medical providers. In this way, the system may enable the technical benefits of sharing access to medical data, while strengthening privacy protections related to usage of the medical data.

It may be appreciated that training machine learning models requires substantial training data. With respect to medical data, it may be infeasible to access sufficient training data to train accurate machine learning models. As an example, to train a machine learning model the generation of datasets may be performed. In the example of medical data, the generated datasets may include medical data with specific features. Identifying locations at which this medical data is stored may present great technological challenges. Indeed, requests may need to be issued to different medical providers, with the requests indicating the specific features of interest. Medical providers may then have to search their stored medical data, and respond to the requests. To ensure privacy, the medical providers may have to perform complex adjustments on identified medical data prior to providing the medical data. For example, all personally identifiable information (PII) may be removed. Once such datasets may have been generated, and thus the included medical data obtained from medical providers, the machine learning model may be trained.

In contrast, machine learning models may be trained with large datasets, and the techniques described herein may ensure that utilized medical data remains private to outsider users. For example, the system may communicate with different compute systems controlled by medical providers. Each medical provider may train a same machine learning model using their respective controlled medical data. Advantageously, the system may route trained machine learning parameters between medical providers. In this way, the system may cause the training of a machine learning model via access to the parameters, hyperparameters, and so on, associated with the model.

In this way, the techniques described herein may describe practical applications related to the enhanced technological utilization of private medical data. Indeed, medical providers may leverage the techniques described herein to enable disparate analyses, computations, and so on, to be performed with their stored medical data. Thus, deep insights may be extracted from medical data while the medical data itself remains secure. Advantageously, the system described herein may provide a front-end for outside users to securely perform the analyses, computations, and so on, described herein. For example, this specification describes enhanced user interfaces which succinctly provide such a front-end. As an example, the user interface may enable rapid specifications of queries from outside users. The user interface may update to present an indication of medical data responsive to a query. Via the same user interface, an outside user may then trigger medical providers storing the indicated medical data to perform requested analyses.

Accordingly, in various embodiments, large amounts of data are automatically and dynamically calculated interactively in response to user inputs, and the calculated data can be efficiently and compactly presented to a user by the system. Thus, in some embodiments, the user interfaces described herein are more efficient as compared to previous user interfaces in which data is not dynamically updated and compactly and efficiently presented to the user in response to interactive inputs.

Further, as described herein, the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

BRIEF DESCRIPTION OF THE DRAWINGS

FIG. 4 illustrates a flowchart of an example process for training a machine learning model according to techniques described herein.

DETAILED DESCRIPTION

Figure 1A:
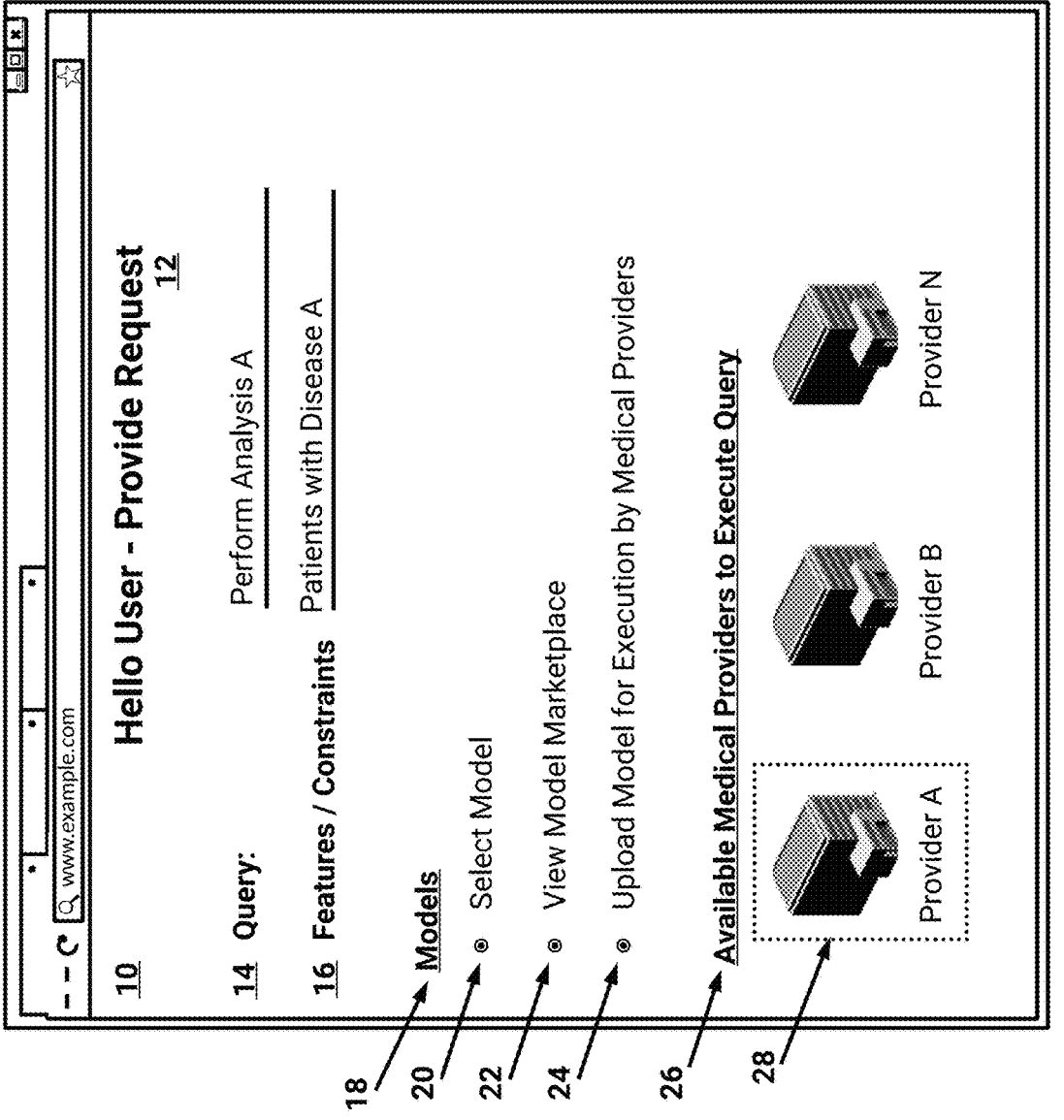
FIG. 1A illustrates an example user interface 10 for triggering execution of a request by an example medical authorization system described herein.

This specification describes one or more technical advantages, and addresses technological problems, associated with extracting insights from medical data while preserving privacy of such medical data. Medical data, in this specification, is to be interpreted broadly. The medical data may be stored in different electronic medical record (EMR) systems or software schemes An example of medical data may include any information generated by medical providers (e.g., doctors, nurses, and so on) regarding a patient. Additional examples of medical data may also include medical images, notes, administrative information (e.g., dates of attendance, medical codes, and so on), and so on. As an example with respect to medical images, the medical data may comprise the two-dimensional or three-dimensional visual information and may also comprise metadata, DICOM imaging information, and so on.

As will be described, a system described herein may serve as a front-end interface to medical data which is privately stored by medical providers. The system may receive requests from entities, and cause execution of the requests via systems controlled by medical providers. The request may indicate one or more models to be utilized for analyzing medical data associated with specified constraints. Thus, the system may enable use of complex models to extract information from medical data. Advantageously, the medical providers may execute the models. In this way, the medical data may remain stored via the medical providers (e.g., remain in situ). Via the technological scheme described herein, analyses based on medical data may be democratized to enable the rapid extraction of deep insights.

As an example, an entity, such as a researcher, may utilize a user interface described herein to generate a request. The system may authorize the entity, for example via a token (e.g., an OAuth token) or other authentication information. The system may then identify medical data that is stored by medical providers which is responsive to the request. For example, and as will be described, the system may generate index information. In this example, the index information may identify locations at which disparate medical data is stored.

Advantageously, the system may ensure that all identified medical data has been affirmatively authorized for use in such analyses. For example, patients may have authorized the use of their medical data. As will be described, the system may optionally analyze agreements executed by patients. Based on these analyses, the system may determine data access rights authorized by the agreements. The request may be routed by the system to the medical providers storing identified medical data. The medical providers may then analyze the medical data according to the request, and route the results to the system for aggregation.

A request, as described above, may identify a model which is to be utilized. For example, the model may analyze medical data to extract insights from the medical data. Example models may include machine learning models, adaptive models, statistical models, data analysis models, behavioral models, or any arbitrary model used to analyze, or extract insights from, medical data. Example statistical models may, as one example, include Bayesian models (e.g., Hierarchical Dirichlet Processes), mixture models, clustering techniques (e.g., k-means clustering), and so on. Example constraints may include features of medical data or patients. Example features may include particular treatment patterns, family history, demographic information, diseases or ailments, genomic information, and so on. The system may analyze a received request, and identify medical providers storing medical data responsive to the request. The system may instruct systems (e.g., compute systems, such as computers with graphics processing units) of the identified medical providers to execute the request. For example, the compute systems may utilize the model with respect to their medical data (e.g., stored, or otherwise controlled, medical data). Upon execution, the system may aggregate results received from the compute systems. These aggregated results may then be presented to the requesting entity.

Furthermore, a request may identify a model (e.g., a machine learning model) which is to be trained utilizing medical data. It may be appreciated that a machine learning model may be defined, at least in part, according to a type of machine learning model and associated hyperparameters. As an example, a neural network may be defined according to a type of units included in the neural network. Example units may include convolutional units, recurrent units, long short-term memory units, gated recurrent units, loss or cost functions, regularization techniques, and so on. Example hyperparameters may describe a structure or form of a neural network. For example, hyperparameters may include a number of layers, a number of neurons, connections between the neurons, activation functions, skip-layer connections, and so on.

With respect to training a machine learning model, the system may identify medical providers storing medical data responsive to a request. The system may then select a first medical providers from among the identified medical providers. The system may provide information describing a machine learning model to be trained to one or more compute systems controlled by the first medical provider. For example, and with respect to a neural network, the system may provide a type of the neural network along with associated hyperparameters. Optionally, the system may provide a range of hyperparameters and the compute systems may train multiple neural networks. As another example, the system may provide code, such as executable or interpretable code, associated with implementation of a neural network. Example code may include TensorFlow code. The compute systems controlled by the first medical provider may then train a machine learning model based on medical data responsive to the request. Upon training, for example up to a particular number of iterations or epochs, the compute systems may provide trained parameters to the system. An example of trained parameters may include weight vectors associated with layers of a neural network. Another example of trained parameters may include bias vectors. It may be appreciated that additional parameters, weights, values, and so on, may be generated.

The system may thus receive the trained parameters from the first medical provider. These trained parameters may be routed to a second of the identified medical providers. The second medical provider may then update the trained parameters utilizing the same machine learning model. For example, compute systems associated with the second medical provider may utilize forward and backward propagation techniques to update the parameters. The system may receive the updated parameters, and continue routing parameters to remaining medical providers. In this way, the system may receive the technical benefit of enhanced training data which may only be achievable through multitudes of medical providers agreeing to their medical data being utilized. Optionally, a last medical provider may generate a validation dataset for utilization with the trained machine learning model.

The user interface, which will be described in more detail with respect to FIG. 1A, may serve as a succinct front-end interface for medical data securely stored by multitudes of medical providers. For example, via simple user input, an entity may rapidly generate a request to be issued to the system for routing to medical providers. The entity may, for example, specify a particular query to be performed. The query may indicate a type of analysis. As an example, an analysis may indicate a type of input and/or output. In this example, an input may indicate particular types of medical data (e.g., medical images, textual notes, and so on) to be utilized. An output may indicate a type of result, such as measurements, labels, and so on. The entity may additionally specify particular features or constraints of medical data or patients. For example, the entity may specify that only patients who have a certain disease are to be utilized for the indicated analysis.

Advantageously, the user interface may enable the easy specification of a model to be utilized for an analysis. Optionally, the entity may select from among existing models or provide their own. In this way, through a simple routine of user input the entity may dramatically reduce barriers associated with implementing complex analyses across previously unavailable datasets stored by different medical providers.

While front-end user interfaces may be utilized to provide queries for execution, the system described herein may additionally expose application programing interfaces (API) for utilization by applications. For example, applications (e.g., 'apps' obtained from electronic application stores, or web applications) may be designed to provide medical analyses to users of the applications. An example application may be designed to provide displayed information at opportunistic times to medical care professionals (e.g., doctors, nurses, and so on). It may be appreciated that a doctor may see multitudes of patients throughout his/her day. While reviewing the medical history of a particular patient, the example application may present insights extracted from analyses performed utilizing hundreds or thousands of patients. As an example, the particular patient may have a particular type of cancer. The application may utilize the APIs to present efficacies of treatment information which is based on analyzing medical data from hundreds or thousands of patients with the same type of cancer.

As will be described, these application may optionally cause the system to implement certain analyses automatically. For example, an application may cause the system to perform an analysis periodically, or upon the system identifying new or updated medical data related to the analysis. In this example, the system may automatically cause different medical providers to perform analyses. The system may then aggregate results from these medical providers.

Optionally, the system may host a particular model which is continuously updated (e.g., substantially continuously, such as periodically). In this way, the particular model may represent a service which may be leveraged. One or more applications may then utilize APIs to access information generated from the particular model. For example, the applications may subscribe to updates from the system. As another example, the applications may query the system periodically.

In all situations in which medical data is authorized for access by an outside entity, the medical data may optionally be assured to have protected health information removed. Example protected health information (PHI) may include the PHI identifiers described in HIPAA. As an example, at least 18 identifiers may be removed.

Example User Interfaces/Block Diagrams

Described below are examples of user interfaces utilized to cause performance of analyses utilizing medical data controlled by different medical providers. The user interfaces may further be utilized to view test results associated with the testing. A requesting device (e.g., the requesting device 120 illustrated in at least FIG. 1B) may present the example user interfaces and receive user input from a user of the requesting device.

Optionally, the user interfaces may be rendered by a browser executing on the requesting device. For example, the user interfaces may be associated with a web application executing on a system (e.g., the medical authorization system 100, or a presentation system in communication with the system 100). The system may be in communication with the requesting device via a network (e.g., the internet). In this example, the system may generate, at least in part, the user interfaces (e.g., user interface information 104 illustrated in FIG. 1B). The requesting device may then render the user interfaces. Additionally, the requesting device may receive user input from the user and route the user input to the system to update the user interfaces.

The user interfaces may also be associated with an application (e.g., an 'app') executing on the requesting device. In this example, the application may render, at least in part, the elements presented in the user interfaces. The system may provide information to the requesting device for inclusion in the user interfaces. For example, the system may provide information indicating medical providers storing responsive medical data. The requesting device may thus receive this provided information and include it in the user interfaces.

The requesting device may include a laptop, tablet, wearable device, computer, augmented or virtual reality system, and so on. Thus, it may be appreciated that the example user interfaces described herein may respond to disparate user input. User input, in this specification, is to be interpreted broadly. For example, user input may encompass textual input. In this example, a user of a user interface may provide text to particular portions of the user interface (e.g., utilizing a keyboard, such as a physical or touch-screen keyboard). As another example, user input may encompass verbal commands. In this example, a requesting device may obtain audio spoken by a user. The requesting device may then analyze the audio, or provide the audio to an outside server system for processing. As another example, user input may encompass touch-screen input. In this example, a requesting device may execute an application which utilizes touch-screen input to trigger requests.

FIG. 1A illustrates an example user interface 10 for triggering execution of a request by an example medical authorization system 100 described herein. The user interface 10, as described above, may represent a user interface included in a web page accessible by a device. As will be described below, with respect to FIG. 1B, a requesting device (e.g., 120) may be in communication with the medical authorization system 100. For example, the communication may be via a network, such as the internet. The user interface 10 may be accessed upon authorization of a user of the user interface 10. As an example, the user may provide a user name and password for authentication by the medical authorization system 100. As another example, the user's requesting device may transmit a token indicating authorization to the system 100. In this example, the user may have previously been authorized and issued a token (e.g., a JSON web token, OAuth 2.0 token, and so on). Thus, an as illustrated in FIG. 1A, an identification of the user may be presented in portion 12.

The user interface 10 includes query portion 14, in which a user of the user interface 10 may indicate a particular analysis to be performed. In the example of FIG. 1A, the user has entered (e.g., via user input) 'Perform Analysis A'. Analysis A may represent a previously defined analysis. For example, utilizing a user interface the user may define parameters, or logic, associated with analysis A. An example of Analysis A may include requesting a number of patients with a certain disease (e.g., multiple myeloma) in a particular geographic area. This example may further be refined (e.g., utilizing portion 16) based on additional features or constraints of patients. Another example of Analysis A may cause determinations as to efficacies of different treatment regiments. In this example, Analysis A may therefore indicate features of medical data to be accessed to determine the efficacy of the treatment regimens. Optionally, Analysis A may be defined utilizing code, or expressions, interpretable by the system 100. Optionally, Analysis A may reference one or more models to be utilized in analyzing medical data or may reference types of models. With respect to referencing types of models, the user may then select from among conforming models (e.g., in portion 18).

Additionally, complex queries may be included by the user in query portion 14. As an example, the user may indicate that 'Analysis A' is to be performed along with 'Analysis B'. In this example, the user may then indicate particular techniques to combine results associated with 'Analysis A' and 'Analysis B'. For example, the user may indicate that values generated from each analysis are to be compared according to one or more mathematical techniques (e.g., variances, averages, and so on).

It may be appreciated that each query may be associated with a respective complexity. Complexity may be determined according to estimated, or actual, computing resource usage, or computing time, required to perform the processing of the query. As will be described, compute systems controlled by one or more medical providers may perform the analyses specified in user interface 10. These compute systems may thus utilize processing resources. In some embodiments, a complexity of each query specified in user interface 10 may thus be determined or estimated. To initiate performance of a query, the user of user interface 10 may be required to provide consideration to the medical providers implementing the query. In this way, the medical providers may be incentivized to process received queries utilizing their stored, or otherwise controlled, medical data.

User interface 10 further includes portion 16, in which the user may specify particular features or constraints. Features or constraints may relate to any filtering which is to be applied to medical data, administrative information, medical images, and so on. In the example of FIG. 1A, the user has specified that the query 14 is to be executed utilizing medical data associated with patients who have 'Disease A'. In the example described above regarding a query to identify a number of patients with a certain disease, portion 16 may be utilized to refine the number. For example, the portion 16 may cause filtering (e.g., removal of) medical data associated with patients who do not satisfy the features or constraints. With respect to the illustration of FIG. 1A, portion 16 may thus identify the number of patients with a certain disease who also have 'Disease A'. Additionally, features or constraints may relate to types of medical data to be utilized. As an example, the user may specify that particular types of medical images are to be utilized when performing an analysis.

Advantageously, the user may utilize portion 18 to select a model for utilization in the analysis (e.g., 'Analysis A'). An example model may be based on the integrated health model initiative (IHMI). In this example, the model may indicate particular features which are to be extracted from medical. For example, an analysis may be utilized to extracts insights related to 'hypertension'. The IHMI model may indicate particular aspects, or pieces, of medical data which relate to 'hypertension'. As illustrated in FIG. 1, the user may provide user input to portion 20 to select a model. For example, the user may have one or more models stored on the user's device. The user may also have one or more models accessible via a network. In this example, the user may indicate a network location associated with a model. Optionally, the system 100 may utilize authentication information associated with the user to access the network location. For example, the network location may correspond to a cloud-storage system or bucket.

The user may further interact with portion 22 to view a model marketplace. It may be appreciated that there may be hundreds, thousands, tens of thousands, of different models. User interface 10 may update to reflect a marketplace of different models. These models may optionally be preferable depending on an analysis being performed. For example, when presenting the model marketplace the user interface 10 may indicate textual information escribing inputs, outputs, and so on, which are associated with each model. Advantageously, the system 100 may utilize the information provided by the user. As an example the system 100 may filter available based on the information. Thus, user interface 10 may present models which may be utilized to perform 'Analysis A'. The model marketplace may additionally include user ratings associated with each model. To select a model from the model marketplace, a measure of consideration may be required.

Optionally, the system 100 may determine one or more suitability measures associated with models included in the model marketplace. As an example, a suitability measure may be based on the query 14 provided by the user. For example, each model may indicate a type of information to be generated. Thus, the system 100 may compare the type of information to be generated with the query. The suitability measure may then be determined based on the comparison. As another example, a suitability measure may be based on a complexity associated with the model. As described above, implementing each request may consume computing resources associated with compute systems controlled by medical providers. Thus, a more complex model may consume greater computing resources. This may result in a greater cost, or consideration, to be provided by the user. The user may therefore prefer, for certain requests, that less complex models be utilized.

The user may also upload a model via portion 24. For example, upon selection of portion 24, the user interface 10 may update to enable selection of a model. The model may be selected from local storage, such as a local drive or local network storage. The model may also be selected from cloud-storage, such as a cloud bucket. Without being constrained by theory, it may be appreciated that models may be of disparate forms or file types. An example of a model may define one or more inputs and one or more outputs. For some models, one or more of the defined inputs may be required for the model to generate output. Optionally, a model may indicate certain inputs which are preferable but not required. With respect to the 'hypertension' described above, a model may therefore indicate information which is required for hypertension. The model may further indicate information which may be advantageous to utilize, but which is not necessary for the model's operation.

Upon receipt of the information provided by the user in the example of FIG. 1, the system 100 has identified medical providers 26 capable of performing the request. For example, the identified medical providers 26 may be determined to store medical data responsive to the request. The user interface 10 may include information identifying the medical providers, such as a name and/or location of each medical provider. In this way, the user of the user interface 10 may utilize the identifications to select one or more medical providers to perform the request. Optionally, the user interface 10 may obfuscate the identified medical providers. For example, the user interface 10 may indicate whether each medical provider is a hospital, research organization, private practice group, and so on. In some embodiments, the system 100 may identify measures associated with scarcity of the responsive medical data. These measures may inform whether, or an extent to which, the user interface 10 includes identifying information associated with the medical providers 26. For example, if the medical data is not common then the user interface 10 may include less, or no, identifying information. As another example, if the medical data is common then the user interface 10 may identifying the medical providers 26

As will be described below, the system 100, or another system (e.g., the secure medical access system 110), may store index information associated with medical data. The index may store locations at which medical data with specific features may be located. For example, the index may indicate locations at which medical images with certain features, metadata, and so on, are located. As another example, the index may indicate locations at which medical data associated with a certain medical condition, or which includes genomic data, and so on, is located. The locations may correspond to medical providers. Thus, the system 100 may utilize the information provided in user interface 10 to identify medical providers storing responsive information. Optionally, a concordance match may be utilized to identify the medical providers. For example, the query 14, features 16, and so on, may be utilized to perform a concordance match. Based on the concordance match with respect to the above-described index, medical providers may be identified.

Optionally, the user interface 10 may present indications of quality metrics associated with the identified medical providers 26. An example quality metric may indicate an extent to which a medical provider stores, or otherwise controls, medical data related to the user's request. In this example, the quality metrics may be greater for a medical provider which stores greater medical data. Another example quality metric may relate to a quality associated with the medical itself. In this example, a quality metric may indicate that a first medical provider captures certain medical data utilizing a known scheme which is superior to that of one or more other medical providers.

For example, the user's request may relate to multiple myeloma. It may be advantageous, for example based on information indicating inputs to a model, that patients' temperature be periodically taken. A first medical provider may be determined to take their patients temperature a first number of times each day (e.g., 7 times). A second medical provider may be determined to take their patients temperature a second number of times each day (e.g., 3 times). The system 100 may therefore assign a higher quality metric to the first medical provider. Advantageously, this quality metric may be automatically learned by the system 100. For example, the system 100 may optionally analyze medical journals or other information indicating best practices or current practices. As another example, the system 100 may learn this quality metric based on user feedback. Users may indicate that the first medical provider stores medical data of a higher quality than the second medical provider.

In the example of FIG. 1A, the user has selected medical provider A 28 to implement the user's request. To indicate the selection, the user interface 10 has updated to highlight, or otherwise call out, medical provider A. For example, a graphical depiction of medical provider A may be shaded, adjusted in color, and so on. In implementations in which the user interface 10 is implemented via conversational audio, the user's requesting device may output audio confirming selection of medical provider A 28. As will be described, the system 100 may then generate information to be provided to the medical provider A 28. For example, compute systems controlled by medical provider A 28 may be instructed to perform the request. In the illustrated example, the compute systems may thus perform 'Analysis A' on medical data associated with patients with 'Disease A' utilizing, at least in part, a model selected utilizing portion 18. While FIG. 1A illustrates a single medical provider being selected, it may be appreciated that the user may select multitudes of medical providers. Optionally, the system 100 may automatically select all, or a threshold number, of medical providers. For example, the system 100 may select the model providers based on the quality metrics described above. In this example, the system 100 may select model providers which store a greatest quantity of medical data responsive to the request. As another example, the system 100 may select the model providers based on capacity, or availability, of compute systems controlled by the model providers.

As described herein, the user interface 10 includes different portions 14-28 associated with interactions by the user. For example, the user may provide input to portions 14-16 to describe an analysis to be performed. The user may optionally select a model in portion 18, such as based on the integrated health model initiative (IHMI) or other proprietary or open source models. It should be appreciated that the portions of user interface 10 may be combined or further separated. As an example, in some embodiments the user may provide a query in a natural language form. In this example, the user may request that the medical authorization system 100, 'determine a percentage of patients who have [disease A] and are taking [pharmaceutical A] who switched to a different pharmaceutical within [time period A].' The system 100 may parse this example request to trigger generation of a request for processing.

Optionally, templates of requests may be utilized by the user. For example, requests may be of a particular form which the user may follow. These templates may be presented to the user in user interface 10. The user may select from among the templates, and include specific elements in the selected template. As an example, a template may include, 'identify a number of patients with [disease]'. In this example, the user may specify the disease. Advantageously, as the user provides user input indicating words, the system 100 may automatically select from among existing templates based on the input. For example, the system 100 may utilize a sequence model, such as a recurrent neural network, to predict a next word the user may enter. Based on these predictions, the system 100 may select a template. As another example, the system 100 may determine measures of similarity between words being provided and words included in templates. For example, a concordance match may be utilized.

Figure 1B:
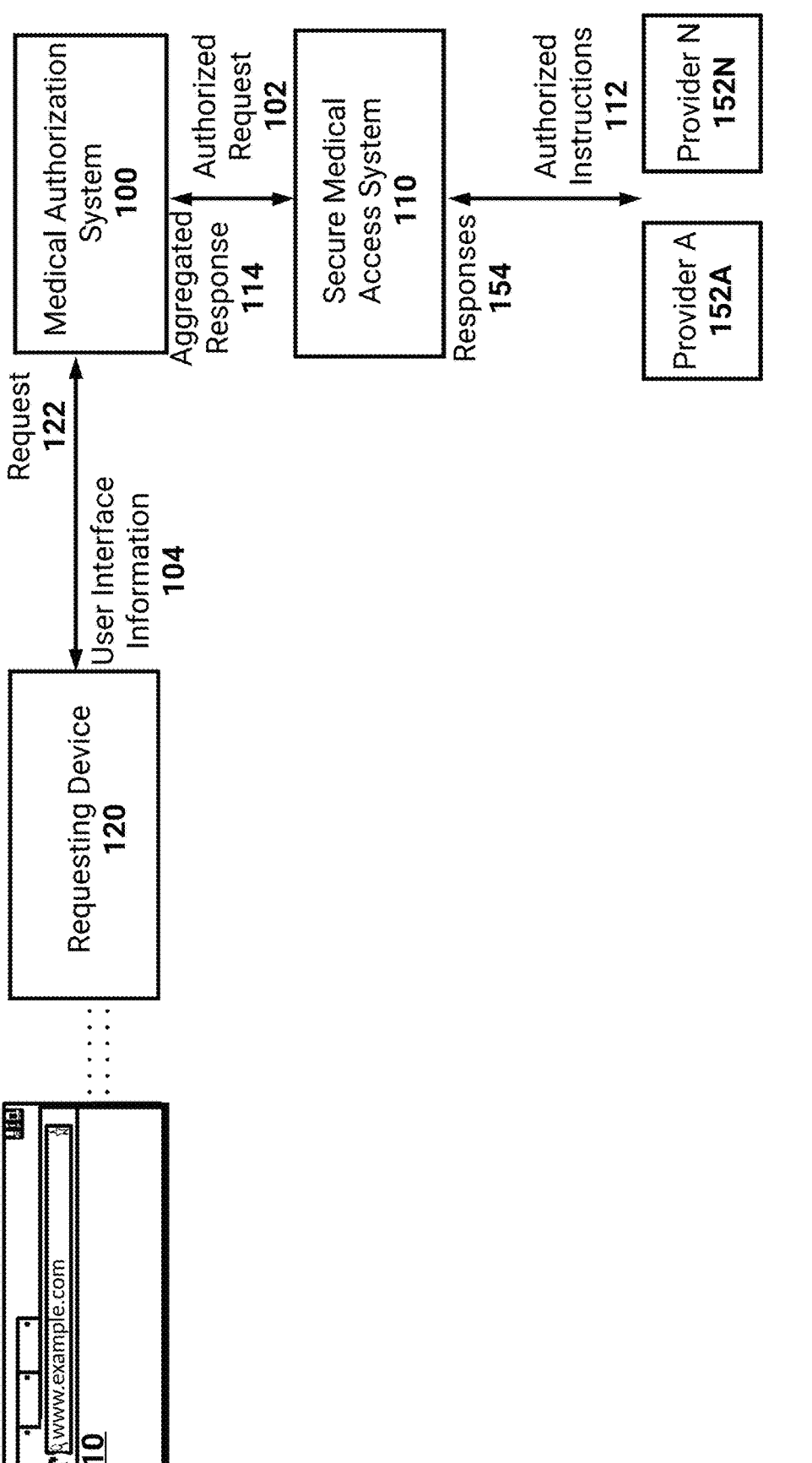
FIG. 1B illustrates an example of the medical authorization system responding to information received from the example user interface.

FIG. 1B illustrates an example of the medical authorization system 100 responding to information received from the example user interface 10. The medical authorization system 100 may be a system of one or more computers or one or more virtual machines executing on a system of one or more computers. As described above, a user may utilize user interface 10 to specify information associated with a request 122. The user interface 10 may optionally be presented, at least in part, by the medical authorization system 100 (e.g., via user interface information 104). In some embodiments, the user interface 10 may be presented via an application executing on the requesting device 120.

As illustrated, a requesting device 120 is presenting user interface 10. In response to information received from the user interface 10, the requesting device 120 has provided request 122 to the medical authorization system 100. The medical authorization system 100 may then identify locations at which medical data responsive to the request 122 is stored. For example, the medical authorization system 100 may utilize one or more indices. The indices may store features of medical data and associated locations. For example, the request may indicate a query associated with multiple myeloma. The medical authorization system 100 may utilize the one or more indices to identify medical providers storing medical data associated with multiple myeloma. As will be described below, the medical authorization system 100 may then cause one or more of these medical providers to implement the request 122.

It may be appreciated that an index may comprise different forms and store information enabling the rapid association of information to storage locations. For example, an inverted index may be utilized to identify specific features of medical data with corresponding storage locations. As another example, a forward index may aggregate features of medical data for one or more documents, medical images, and so on, stored by a medical provider. As another example, an index may be associated with an Elasticsearch engine.

While the description above focused on the medical authorization system 100 storing indices, in some embodiments the system 100 may provide requests to different medical providers. For example, the system 100 may provide a request to a medical provider identifying the specified information in the request 122. The medical provider may then provide information confirming whether it stores responsive medical data.

The medical authorization system may then generate an authorized request 102 to be provided to a secure medical access system 110. The secure medical access system 100 may then provide information to, and receive information from, medical providers (e.g., providers 152A-152N). The secure medical access system 110 may be a system of one or more computers, one or more virtual machines executing on a system of one or more computers, and so on. Optionally, the secure medical access 110 may be part of the medical authorization system 100. For example, the secure medical access system 110 may represent a secure module, or software engine, which is executing on the medical authorization system 100.

The authorized request 102 provided to the secure medical access system 100 may include information associated with the request 122. The authorized request 102 may further indicate one or more medical providers to implement the request 122. For example, the one or more medical providers may be selected via the user interface 10. As another example, the one or more medical providers may be automatically selected as described above. The secure medical access system 110 may then generate authorized instructions 112 to be provided to medical providers 152A-N. Advantageously, the authorized request 102 may include authentication information associate with the medical authorizations system 100. For example, a secure token may be utilized. As another example, the authorized request 102 may be signed utilizing a public key/private key scheme.

It may be appreciated that separating a system which communicates with outside devices (e.g., device 120), from a system which communicates with medical providers, may provide technical advantages. As an example, the medical authorization system 100 may represent a front-end system. The secure medical access system 110 may thus securely communicate with medical providers and route information to the system 100. In this way, outside devices or systems may be unable to directly interface with the medical providers. In some embodiments, the medical authorization system 100 may store index information identifying locations at which medical data is stored. In some other embodiments, the index information may indicate unique identifiers associated with the locations. In these embodiments, the secure medical access system 110 may receive the unique identifiers from the medical authorization system 100. The secure medical access system 110 may store mapping information to translate between a unique identifier and a specific medical provider. In this way, the secure medical access system 110 may be utilized to securely instruct medical providers to implement the user's request 122.

As described above, and as illustrated, the secure medical access system 110 may provide authorized instructions 112 to the medical providers 152A-N. The authorized instructions 112 may be provided to compute systems associated with each medical provider. The compute systems may then access specific medical data based on the authorized instructions 112. For example, the specific medical data may be identified based on the user's request 122. The compute systems may implement the authorized instructions 112, such performing computations associated with one or more models.

The secure medical access system 110 may then receive responses 154 from the medical providers 152A-N. These responses 154 may then be aggregated to combine information included in the responses 154. For example, the information in the responses may be summed. As another example, the information may be averaged. As another example, the information may be combined according to one or more models. For example, the user may specify the utilization of one or more models. In this way, the secure medical access system 100 may generate an aggregate response. The aggregated response may then be provided to the medical authorization system 100 for routing to the requesting device 120.

Optionally, the medical authorization system 100 may store the aggregated response 114. For example, the system 100 may store the aggregated response 114 in one or more databases controlled by, or otherwise accessible to, the medical authorization system 100. As another example, the aggregated response 114 may be stored in cloud-based storage (e.g., a cloud storage bucket). The aggregated response 114 may be encrypted according to one or more schemes. For example, the medical authorization system 100 may utilize a public key received from the requesting device 120 to encrypt the aggregated responses. The encrypted version of the aggregated response 114 may then be stored in cloud-storage, which is accessible to, or controlled by, the user of the requesting device 120.

As will be described, with respect to at least FIG. 1C, the medical authorization system 100 may utilize application programming interfaces (APIs) to interface with outside systems or devices. For example, an application may utilize the APIs to request that the system 100 determine certain insights from medical data associated with different medical providers. In this example, users of the application may thus be presented with insights associated with requests generated by the application. Advantageously, the system 100 may periodically determine updates to the insights. These updates may then be cached by the system 100. In this way, the insights may represent a service implemented by the system 100 which is accessible to outside users via the application.

Figure 1C:
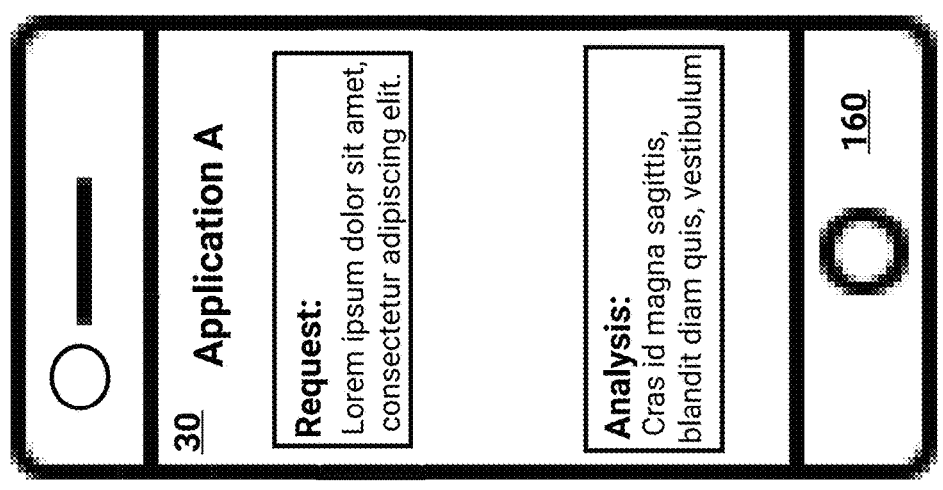
FIG. 1C illustrates an example application executing on an example user device.

FIG. 1C illustrates an example application 30 executing on an example user device 160. As described in FIG. 1A, an example user interface 10 may be utilized to generate a request. It may be appreciated that the medical authorization system 100 may respond to application programming interface (API) calls associated with APIs. Thus, different applications may be customized and/or generated which leverage these APIs. In this way, different user interfaces may be employed which are configured to enable users to provide requests to the medical authorization system 100. For example, FIG. 1C illustrates user interface 30 presented via a mobile application (e.g., an 'app') executing on user device 160.

In some embodiments, the medical authorization system 100 may cause a particular application, or request, to be implemented as a service to users. For example, a particular request may be associated with identifying a number of patients who exhibit certain features. In this example, the medical authorization system 100 may cause request to be implemented as a service. Users may thus subscribe to updates related to this request. Optionally, the medical authorization system 100 may store information associated with the request. Thus, the system 100 may periodically request that an updated number be ascertained by medical providers. As another example, an application may represent a web application. For example, the web application may execute via the system 100 or via an outside cloud-system. The web application may then provide requests to the medical authorization system 100. Users may access the web application, and view results associated with one or more requests.

Example Block Diagram

Figure 2:
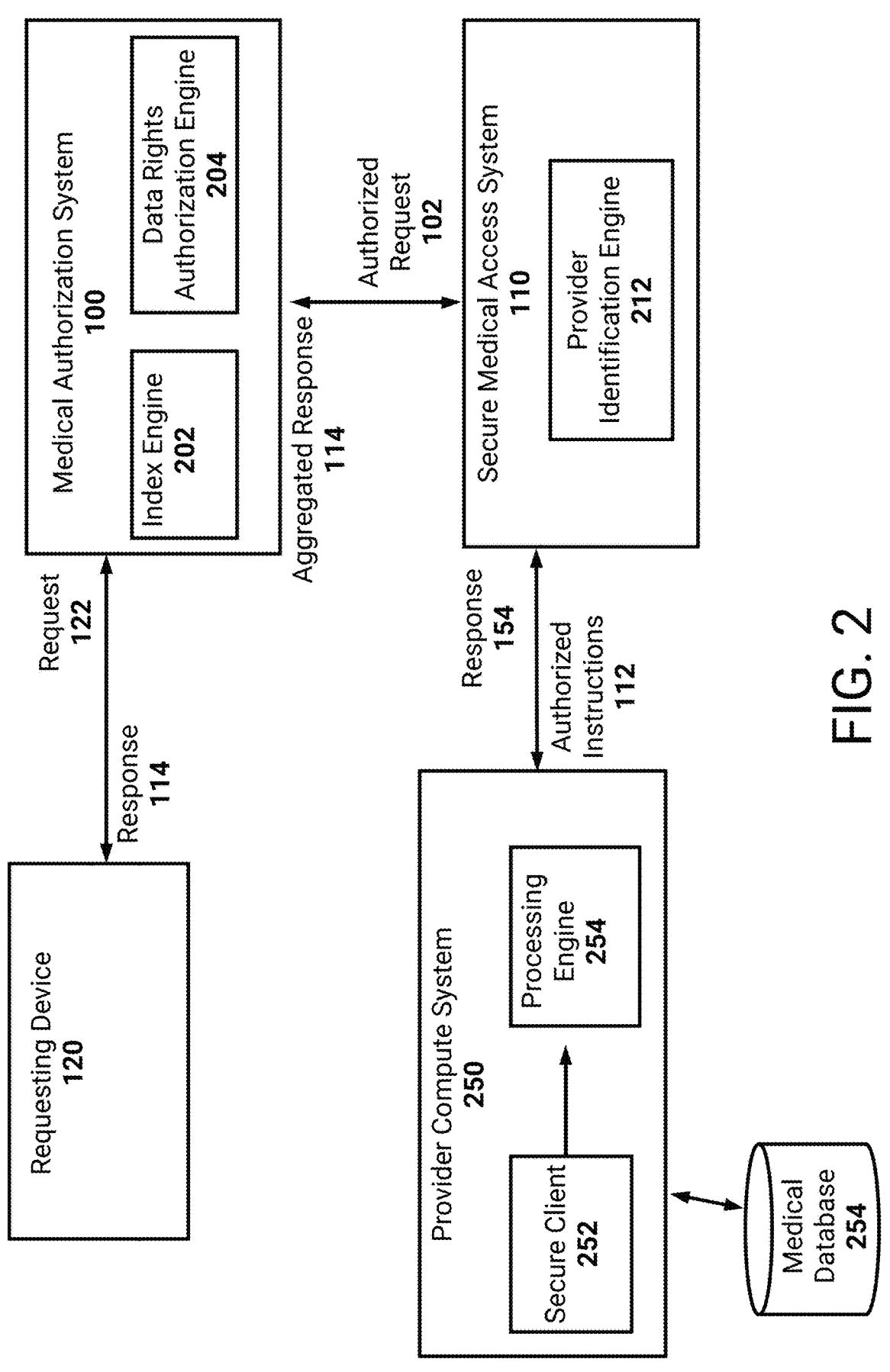
FIG. 2 illustrates a block diagram of an example medical authorization system.

FIG. 2 illustrates an example of a medical authorization system 100. As described in FIG. 1B, the medical authorization system 100 may respond to requests for insights into medical data. For example, the medical authorization system 100 may receive a request 122 from a requesting device 120, and cause the secure medical access system 110 to provide authorized instructions 112 to one or more compute systems. For example, provider compute system 250 is illustrated as receiving the authorized instructions 112. The authorized instructions 112 may cause the provider compute system 250 to perform an analysis based on a specified, or provided, model. The instructions 112 may also cause the provider compute system 250 to train, at least in part, a machine learning model. In response to the instructions 112, the provider compute system 250 may then provide a response 112 associated with the request 122. The response 112, optionally along with other responses from other provider compute systems, may then be aggregated 114 and routed to the requesting device 120.

As illustrated in FIG. 2, the medical authorization system 100 includes an index engine 202. As described in FIG. 1B, the medical authorization system 100 may store one or more indices indicating locations at which particular medical data is stored. For example, the indices may indicate that medical data associated with certain forms of rare cancer are stored by particular medical providers. Optionally, the medical authorization system 100 may cause the crawling of medical data stored by medical providers. For example, medical providers may utilize compute systems to crawl their stored medical data. The crawlers may generate index information, such as inverted indices, and provide the index information to the medical authorization system 100 (e.g., optionally via the secure medical access system 100). An example index may therefore indicate a feature (e.g., a medical condition, a portion of a body implicated, a discrete feature of a medical history, and so on) along with one or more medical providers which store medical data implicating the feature.

The medical authorization system 100 further includes a data rights authorization engine 204. The data rights authorization engine 204 may ensure that medical data which is responsive to the request 122, is authorized for use in responding to the request. For example, it may be appreciated that patients may have different data rights agreements in place with medical providers. An example data rights agreement may indicate that a patient's medical data may be utilized for certain purposes. As an example, the agreement may indicate that the medical data may be utilized to perform analyses. In this example, the agreement may indicate that all protected health information (PHI) is removed prior to use. As described in U.S. Patent Pub. No. 2020/0034563, which is incorporated herein by reference, data rights agreements may be ingested by a system. The system may therefore ascertain how medical data may be used. Thus, the medical authorization system 100 may utilize this information to inform which medical providers are to be instructed to implement the request 122. In some embodiments, the secure medical access system 110 may store this data rights information. In some embodiments, compute systems associated with medical providers may store the data rights information. In these embodiments, the compute systems may thus automatically only utilize medical data which is in compliance with the data rights agreements. Optionally, the compute systems 100 may reject authorized instructions 112, at least in part, if they cannot be completed due to violating the data rights agreements.

The secure medical access system 110 includes a provider identification engine 212. The engine 212 may enable the secure medical access system 100 to provide instructions 112 to specific compute systems. For example, the authorized request 102 received from the medical authorization system 100 may indicate specific medical providers. The request 102 may also indicate unique identifiers associated with medical providers. The engine 212 may therefore identify network locations of compute systems controlled by the indicated medical providers. The engine 212 may then provide authorized instructions 112 to the compute systems for processing. The instructions 112 may include authorization information, such as an encrypted token, information signed according to a public key/private key scheme, and so on.

The provider compute system 250 may be a system of one or more computers, a system of one or more virtual machines executing on a system of one or more computers, and so on. Advantageously, the provider compute system 250 may comprise substantially high-performance components. Some compute systems may include graphics processing units, tensor processing units, and so on. As an example, it may be appreciated that training a machine learning model may include substantial processing. For example, large vectors or matrices of training data may be routinely processed according to forward and backward propagation schemes. Thus, the provider compute system 250 may comprise processing elements which can rapidly perform such mathematical operations (e.g., graphics processing units).

As illustrated the provider compute system 250 includes a secure client 252. In some embodiments, the secure client 252 may respond to information from the secure medical access system 110. For example, the secure client may interface with the system 110 to ensure that only instructions 112 received from the system 110 are implemented. The secure client 252 may optionally provide instructions to a processing engine 254. In some other embodiments, the processing engine 254 may communicate with the secure medical access system 100. The processing engine 254 may perform the processing indicated in the authorized instructions 112. For example, the instructions 112 may identify that that a particular model be utilized with respect to medical data associated with one or more constraints. The processing engine 254 may therefore access medical data (e.g., stored in a database 254), and process the medical data according to the particular model. Based on the processing, the provider compute system 250 may provide a response 154 to the secure medical access system 110.

Optionally, one or more request and/or models may be implemented as a service to which users may subscribe or access. For example, one or more medical providers may be incentivized to cause a particular request to be updated. In this example, the particular request may be updated periodically or based on the occurrence of new medical data. As an example, a request may cause an identification of a number of patients with certain constraints to be determined. Thus, provider compute systems may monitor for any updates to this number. The updates may be provided to the secure medical access system 100.

In some embodiments, the medical authorization system 100, and/or secure medical access system 110, may cache results associated with received requests. Certain requests may be commonly received (e.g., greater a threshold number of times or at greater than a particular frequency). Thus, the medical authorization system 100 may cache the results to avoid causing the compute systems to re-perform the requests. Optionally, the medical authorization system 100 may ensure that the analyses are fresh. For example, the system 100 may ensure that the medical data which was relied upon to generate the cached result has not changed. In this example, the system 100 may request that the secure medical access system 110 identify whether the medical data has changed. For example, the secure medical access system 100 may provide requests to the compute systems. The provided requests may cause the compute systems to identify whether any medical data utilized to generate a response has substantively changed or whether there is new medical data. Optionally, a request may be re-performed if greater than a threshold amount of new medical data has been identified since a prior response was generated.

Example Flowcharts

Figure 3:
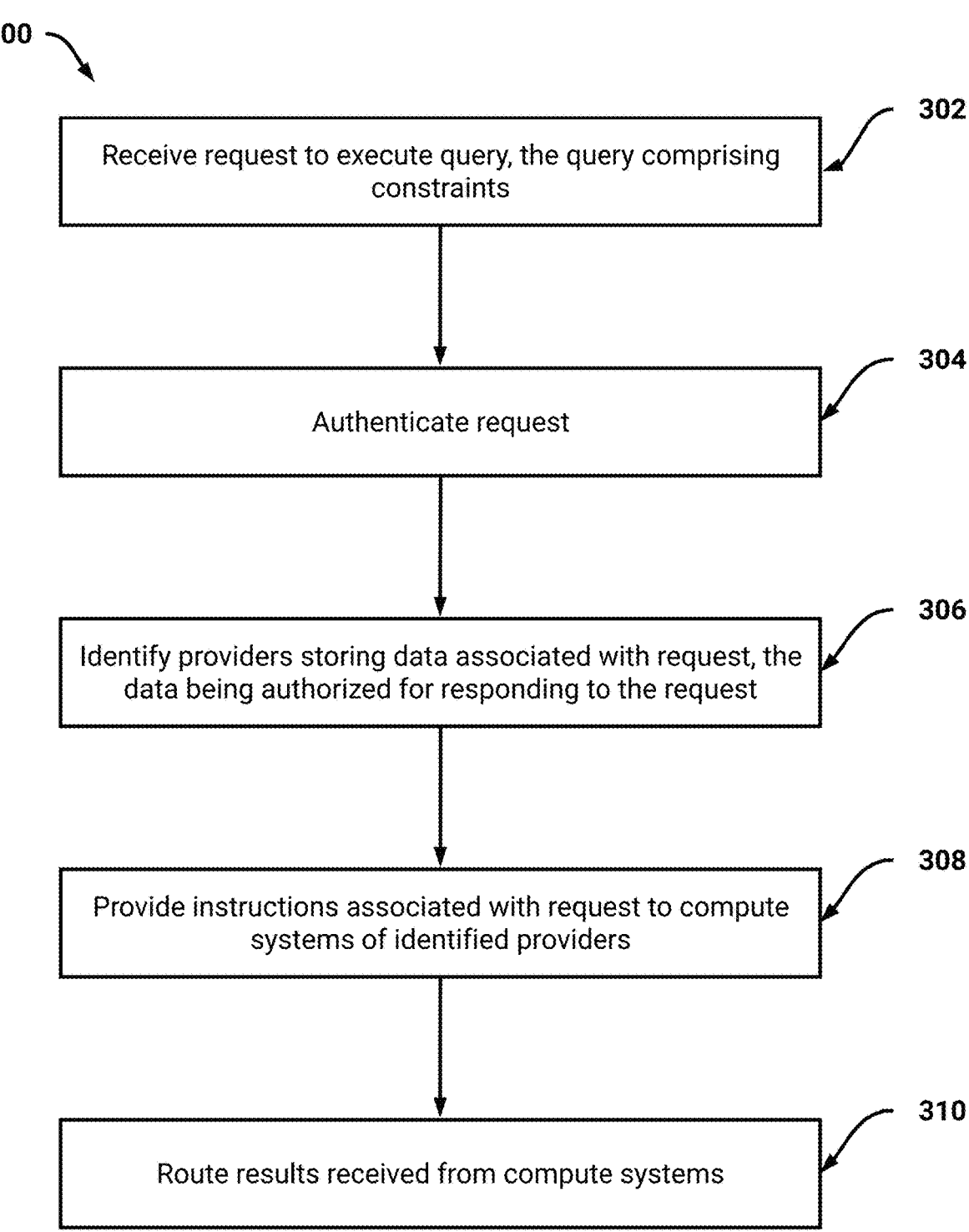
FIG. 3 illustrates a flowchart of an example process for responding to a request associated with medical data stored by one or more medical providers.

FIG. 3 illustrates a flowchart of an example process 300 for responding to a request associated with medical data stored by one or more medical providers. For convenience, the process 300 will be described as being performed by a system of one or more computers (e.g., the medical authorization system 100 and/or the secure medical access system 110).

At block 302, the system receives a request to execute a query. As described in FIGS. 1A-1C, the request may be received from a user device. For example, a user of the user device may utilize an application to generate the request. In some embodiments, the system may receive the request from an application (e.g., web application), device, or system, utilizing one or more APIs. The query to be executed may comprise certain constraints. For example, the query may indicate that certain types of medical data are to be utilized to perform the request. Optionally, the request may indicate a particular model to be utilized. As described in FIG. 1A, the model may be selected by a user from amongst a multitude of available models or may be provided by the user.

At block 304, the system authenticates the request. With respect to a user device, the request may be authenticated based on authentication information associated with a user of the user device. For example, an encrypted token may be provided in the request. As another example, a user name/ password of the user may be received. With respect to an application, the application may provide an encrypted token indicating that the application is authorized to provide requests. The application may further sign the request according to a public key/private key scheme.

At block 306, the system identifies medical providers storing data associated with the request. The system may utilize one or more indices to identify medical providers storing medical data which may be utilized to respond to the request. As described in U.S. Patent Pub. No. 2020/0034563, which is incorporated herein by reference, the stored medical data may further be validated to ensure that it comports with data rights agreements executed by patients, medical professionals, and so on. In this way, all requests which are serviced by the system may be ensured to be in agreement with explicit permissions.

At block 308, the system provides instructions to compute systems associated with the identified providers. The system may route the request to the compute systems for implementation. For example, the compute systems may perform the query and/or model indicated in the request.

At block 310, the system routes results received from the compute systems. The system may receive different results from the compute systems and may optionally perform an aggregation process to combine the results. With respect to a user device, the results may be routed to the user device (e.g., for presentation or storage). With respect to an application providing information via APIs, the system may route the results to the application via the APIs. In some embodiments, the system may cache the results to rapidly respond to future requests.

FIG. 4 illustrates a flowchart of an example process 400 for training a machine learning model according to techniques described herein. For convenience, the process 400 will be described as being performed by a system of one or more computers (e.g., the medical authorization system 100 and/or the secure medical access system 110).

At block 402, the system receives a request. In the example of FIG. 4, the request indicates features of medical data and a machine learning model which is to be trained based on the medical data. For example, information describing a neural network may be identified. In this example, hyperparameters of the neural network may be specified. A type of neural network may also be specified (e.g., convolutional neural network, recurrent neural network, and so on). Optionally, the hyperparameters may indicate features of the layers of the neural network, such as a convolutional layer, a pooling layer, a type of pooling layer, and so on.

At block 404, the system identifies medical providers storing medical data associated with the request. Similar to the description of FIG. 3, the system utilizes one or more indices to identify the medical providers. The system may also ensure that the medical data stored by the medical providers is authorized to be utilized. For example, the medical data may be identified as being authorized to train machine learning models.

At block 406, the system provides instructions to one or more compute systems of a first medical provider. The instructions may cause the compute systems to train a machine learning model as described in the request.

At block 408, the system receives parameters associated with the machine learning model from the compute systems. For example the parameters may comprise weight matrices, bias matrices, and so on.

At block 410, the system determines whether an additional medical provider was identified. If there is another medical provider, the system routes the trained parameters to compute systems associated with the other medical provider. The other medical provider may then utilize its stored medical data as training data to update the weight matrices, bias matrices, and so on.

At block 412 the system routes the trained machine learning model if there are no additional medical providers. The trained machine learning model may be routed according to the parameters trained as per the blocks above.

Figure 5:
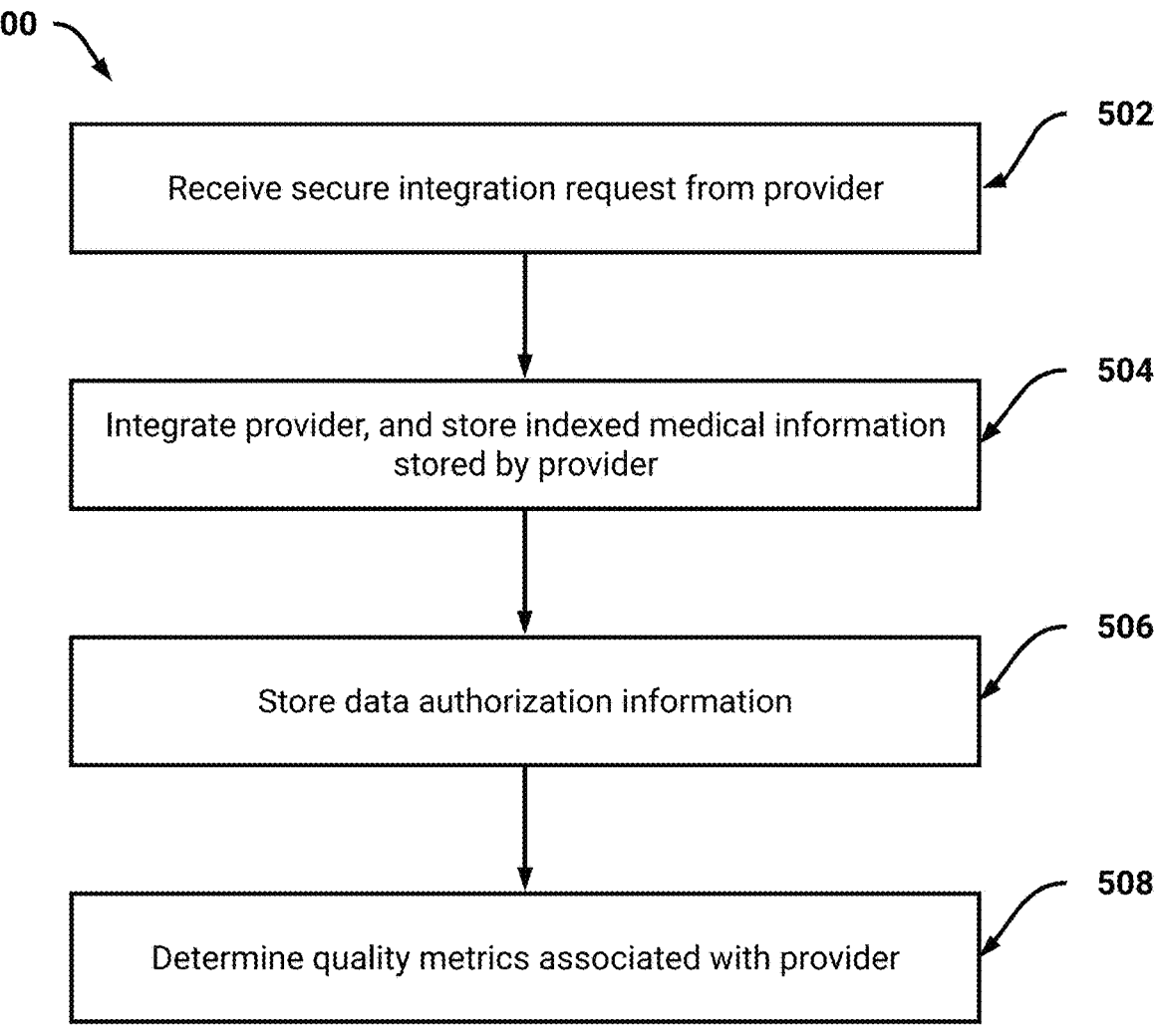
FIG. 5 illustrates a flowchart of an example process for an example medical authorization system integrating with an example medical provider.

FIG. 5 illustrates a flowchart of an example process 500 for an example medical authorization system integrating with an example medical provider. For convenience, the process 500 will be described as being performed by a system of one or more computers (e.g., the medical authorization system 100 and/or the secure medical access system 110).

At block 502, the system receives a secure integration request from a medical provider. It may be appreciated that medical providers may prefer to integrate with the system, to enable the complex insights into medical described herein. Thus, the medical provider may cause software, or an application, associated with the system to be executed on compute systems the medical provider controls. For example, the software or application may be configured to provide the integration request to the system.

At block 504, the system integrates the medical provider. For example, the system may store network location information associated with the compute systems. In this way, the system may provide instructions to the compute systems to implement requests. The system may also store a public key associated with the medical provider. The system may also receive index information generated by the compute systems. Optionally, the software or application executing on the compute systems may automatically crawl medical data stored by the medical provider. For example, electronic medical record (EMR) systems may be accessed, and information stored therein crawled. As another example, laptops or computers of medical professionals, medical imaging systems, and so on, may additionally be crawled.

At block 506, the system optionally stores data authorization information. Optionally, the system may receive indications of data rights agreements made by the medical provider with patients, medical professionals, and so on as described in U.S. Patent Pub. No. 2020/0034563.

At block 508, the system determines quality metrics associated with provider. As described in FIG. 1A, the system may determine measures associated with the medical data stored by the medical provider. For example, the system may ascertain a frequency with which certain measurements are made. As another example, the system may compare the medical data to the integrated medical health initiative (IHMI) model. In this example, the system may identify the types of medical data which the IHMI indicates as being associated with specific diseases, treatment plans, and so on. The system may then determine a quality measure based on whether the medical data follows the IHMI. For example, the IHMI model may indicate that for a particular disease or treatment plan, certain types of medical data are required to be utilized, monitored, and so on. The system may therefore ensure that the required types are represented in the medical data. The IHMI may further indicate that other types of medical data are beneficial or useful. Thus, a quality measure may be increased if the medical provider ensures that the other types are represented in the medical data.

Example System

Figure 6:
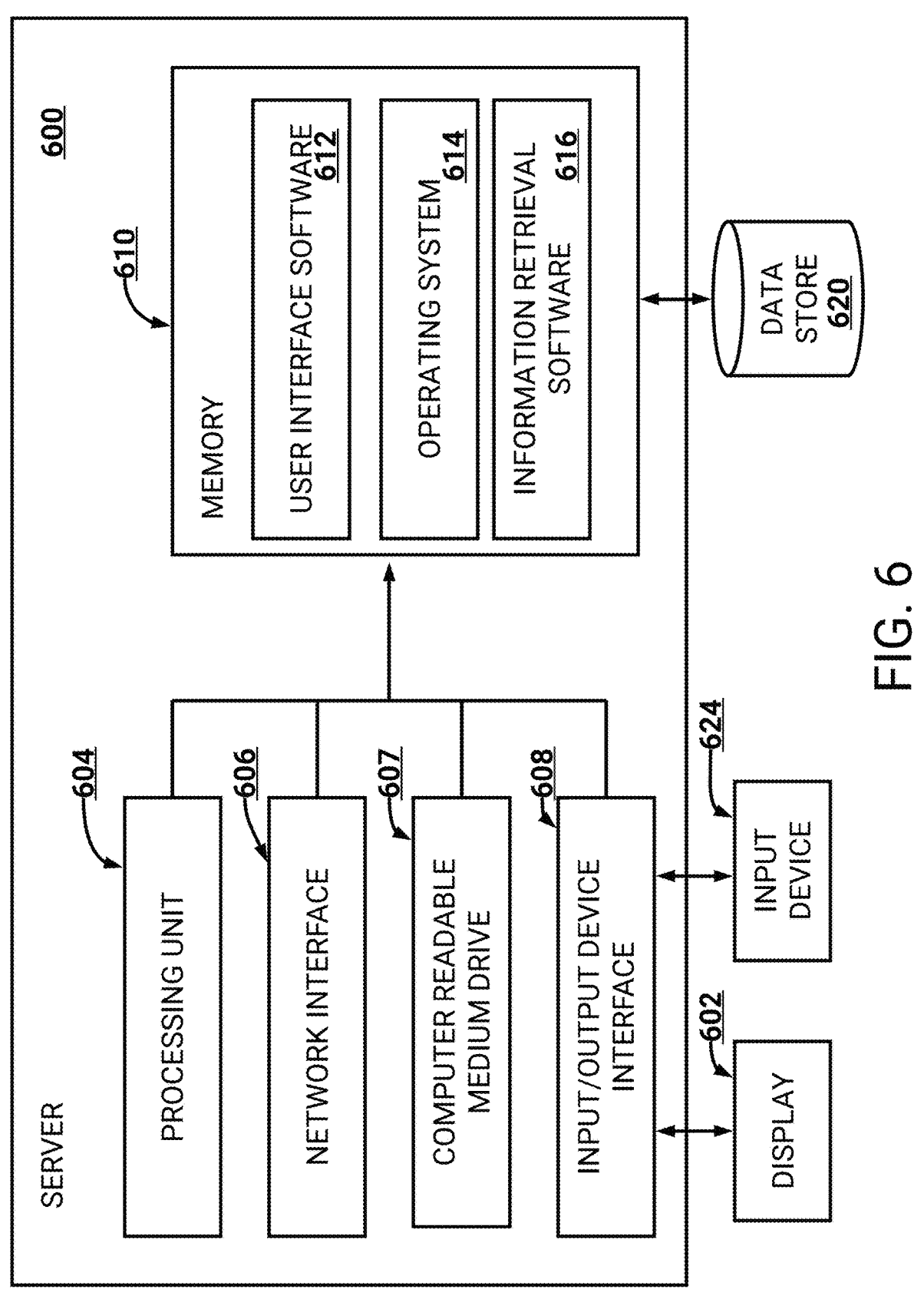
FIG. 6 is a block diagram depicting an illustrative configuration of one embodiment of a server that may implement one or more of the systems described herein.

FIG. 6 is a block diagram depicting an illustrative configuration of one embodiment of a server 600 that may implement elements of the medical authorization system 100 and/or secure medical access system 110. The general architecture of server 600 depicted in FIG. 6 includes an arrangement of computer hardware and software components that may be used to implement aspects of the present disclosure. As illustrated, the server 600 includes a processing unit 604, a network interface 606, a computer readable medium drive 607, an input/output device interface 620, a display 602, and an input device 624, all of which may communicate with one another by way of a communication bus. The network interface 606 may provide connectivity to one or more networks or computing systems, such as to one or more clients, indexing systems, data storage systems, and so on. The processing unit 604 may thus receive information and instructions from other computing systems or services via a network. The processing unit 604 may also communicate to and from memory 610 and further provide output information for an optional display 602 via the input/output device interface 620. The input/output device interface 620 may also accept input from the optional input device 624, such as a keyboard, mouse, digital pen, etc. In some embodiments, the server 600 may include more (or fewer) components than those shown in FIG. 6. For example, some embodiments of the server 600 may omit the display 602 and input device 624, while providing input/output capabilities through one or more alternative communication channel (e.g., via the network interface 606).

The memory 610 may include computer program instructions that the processing unit 604 executes in order to implement one or more embodiments. The memory 610 generally includes RAM, ROM, and/or other persistent or non-transitory memory. The memory 610 may store an operating system 614 that provides computer program instructions for use by the processing unit 604 in the general administration and operation of the server 600. The memory 610 may further include computer program instructions and other information for implementing aspects of the present disclosure. For example, in one embodiment, the memory 610 includes user interface software 612 that generates user interfaces (and/or instructions therefor) for display upon a computing device, e.g., via a navigation interface such as a web browser installed on the computing device. In addition, memory 610 may include or communicate with one or more auxiliary data stores, such as data store 620, which may correspond to any persistent or substantially persistent data storage, such as a hard drive (HDD), a solid-state drive (SDD), network attached storage (NAS), a tape drive, or any combination thereof.

In addition to the user interface module 612, the memory 610 may include information retrieval software 616 that may be executed by the processing unit 604. In one embodiment, the information retrieval software 616 implements various aspects of the present disclosure. For example, determining ML models and proposing blocks for inclusion in a blockchain. As another example, evaluating proposed blocks and committing, or not committing, the proposed blocks into the blockchain. While the information retrieval software 616 is shown in FIG. 6 as part of the server 600, in other embodiments, all or a portion of the software may be implemented by alternative computing devices, such as virtual computing devices within a hosted computing environment.

Each of the processes, methods, and algorithms described in the preceding sections may be embodied in, and fully or partially automated by, code modules executed by one or more computer systems or computer processors comprising computer hardware. The code modules (or "engines") may be stored on any type of, one or more, non-transitory computer-readable media (e.g., a computer storage product) or computer storage devices, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, for example, volatile or non-volatile storage.

In general, the terms "engine" and "module," as used herein, refer to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on one or more computer readable media, such as compact discs, digital video discs, flash drives, or any other tangible media. Such software code may be stored, partially or fully, on a memory device of the executing computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

User interfaces described herein are optionally presented (and user instructions may be received) via a user computing device using a browser, other network resource viewer, a dedicated application, or otherwise. Various features described or illustrated as being present in different embodiments or user interfaces may be combined into the same embodiment or user interface. Commands and information received from the user may be stored and acted on by the various systems disclosed herein using the processes disclosed herein. While the disclosure may reference to a user hovering over, pointing at, or clicking on a particular item, other techniques may be used to detect an item of user interest. For example, the user may touch the item via a touch screen, or otherwise indicate an interest. The user interfaces described herein may be presented on a user terminal, such as a laptop computer, desktop computer, tablet computer, smart phone, virtual reality headset, augmented reality headset, or other terminal type. The user terminals may be associated with user input devices, such as touch screens, microphones, touch pads, keyboards, mice, styluses, cameras, etc. While the foregoing discussion and figures may illustrate various types of menus, other types of menus may be used. For example, menus may be provided via a drop-down menu, a tool bar, a pop-up menu, interactive voice response system, or otherwise.

The various features and processes described herein may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y or Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y or at least one of Z to each be present.

While certain example embodiments have been described, these embodiments have been presented by way of example only, and are not intended to limit the scope of the disclosure. Thus, nothing in the foregoing description is intended to imply that any particular element, feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated herein, it should be noted that the use of particular terminology when describing certain features or aspects of the invention should not be taken to imply that the terminology is being re-defined herein to be restricted to including any specific characteristics of the features or aspects of the invention with which that terminology is associated.

What is claimed is:

1. A computer system comprising one or more computer processors configured to execute software code to perform operations comprising:

receiving a request associated with analyzing medical data, the request specifying one or more constraints, wherein the request includes authorization information and a model, wherein the model includes a machine learning model or statistical model for application to medical data responsive to the request;

accessing index information, wherein the index information indicates network locations associated with the compute systems, and identifying a plurality of medical providers storing respective subsets of medical data responsive to the request, wherein the computer system does not have access to the respective subsets of medical data;

instructing, for each medical provider based on the request, individual compute systems controlled by individual medical providers to perform the request, wherein the computer system uses the authorization information to authenticate the request and authorize instructions transmitted to the individual compute systems, wherein individual compute systems apply the model to individual subsets of medical data stored by the individual medical providers, wherein the model is transmitted to the individual compute systems;

receiving, from the medical providers, results associated with the request, and aggregating the results, wherein the results reflect, at least, output associated with the model, and wherein the output includes one or more of measurements or labels; and providing the aggregated results in response to the request.

2. The computer system of claim 1, wherein the index information is generated by the compute systems associated with the medical providers.

3. The computer system of claim 1, wherein individual compute systems are configured to crawl electronic medical record systems associated with individual medical providers.

4. The computer system of claim 1, wherein the aggregated results indicate one or more insights extracted from the aggregation of the subsets of medical data.

5. The computer system of claim 1, wherein the model is a machine learning model.

6. The computer system of claim 1, wherein the request is received via an interactive user interface, wherein the interactive user interface receives one or more queries which utilize the constraints, wherein the computer system determines a complexity associated with the queries which estimates computing resource usage associated with the compute systems, and wherein the interactive user interface presents the determined complexity.

7. The computer system of claim 1, wherein the request is received via an interactive user interface presenting information identifying a plurality of models, and wherein the interactive user interface:

receives selection of the model from the plurality of models, and presents graphical identifiers associated with the identified medical providers.

8. The computer system of claim 7, wherein the operations further comprise:

generating respective suitability measures associated with the plurality models, wherein individual suitability measures reflect suitability of an individual model to the request.

9. The computer system of claim 8, wherein the suitability measures are further based on complexities associated with the models, the complexities being based on computing resource usage associated with the request.

10. A method implemented by a system of one or more processors, the method comprising:

receiving a request associated with analyzing medical data, the request specifying one or more constraints, wherein the request includes authorization information and a model, wherein the model includes a machine learning model or statistical model for application to medical data responsive to the request;

accessing index information, wherein the index information indicates network locations associated with the compute systems, and identifying a plurality of medical providers storing respective subsets of medical data responsive to the request, wherein the computer system does not have access to the respective subsets of medical data;

instructing, for each medical provider, individual compute systems controlled by individual medical providers to perform the request, wherein the computer system uses the authorization information to authenticate the request and authorize instructions transmitted to the individual compute systems, wherein individual compute systems apply the model to individual subsets of medical data stored by the individual medical providers, wherein the model is transmitted to the individual compute systems with the request;

receiving, from the medical providers, results associated with the request, and aggregating the results, wherein the results are based on output from the model, wherein the output includes one or more measurements or labels;

providing the aggregated results in response to the request.

11. The method of claim 10, wherein the index information is generated by the compute systems associated with the medical providers.

12. The method of claim 10, wherein individual compute systems are configured to crawl electronic medical record systems associated with individual medical providers.

13. The method of claim 10, wherein the aggregated results indicate one or more insights extracted from the aggregation of the subsets of medical data.

14. The method of claim 10, wherein the model is a machine learning model.

15. The method of claim 10, wherein the request is received via an interactive user interface, wherein the interactive user interface receives one or more queries which utilize the constraints, wherein the computer system determines a complexity associated with the queries which estimates computing resource usage associated with the compute systems, and wherein the interactive user interface presents the determined complexity.

16. Non-transitory computer storage media storing instructions that when executed by a system of one or more processors, cause the one or more processors to perform operations comprising:

receiving a request associated with analyzing medical data, the request specifying one or more constraints, wherein the request includes authorization information and a model, wherein the model includes a machine learning model or statistical model for application to medical data responsive to the request;

accessing index information, wherein the index information indicates network locations associated with the compute systems, and identifying a plurality of medical providers storing respective subsets of medical data responsive to the request, wherein the computer system does not have access to the respective subsets of medical data;

instructing, for each medical provider, individual compute systems controlled by individual medical providers to perform the request, wherein the computer system uses the authorization information to authenticate the request and authorize instructions transmitted to the individual compute systems, wherein individual compute systems apply the model to individual subsets of medical data stored by the individual medical providers, wherein the model is transmitted to the individual compute systems with the request;

receiving, from the medical providers, results associated with the request, and aggregating the results, wherein the results are based on output of the model, wherein the output includes one or more measurements or labels;

providing the aggregated results in response to the request.

17. The computer storage media of claim 16, wherein the aggregated results indicate one or more insights extracted from the aggregation of the subsets of medical data.

18. The computer storage media of claim 16, wherein the request is received via an interactive user interface, wherein the interactive user interface receives one or more queries which utilize the constraints, wherein the computer system determines a complexity associated with the queries which estimates computing resource usage associated with the compute systems, and wherein the interactive user interface presents the determined complexity.

\* \* \* \* \*